(12) United States Patent
Kelly

(10) Patent No.: US 6,706,928 B2
(45) Date of Patent: Mar. 16, 2004

(54) ALDOL CONDENSATION REACTION AND CATALYST THEREFOR

(75) Inventor: Gordon J Kelly, Darlington (GB)

(73) Assignee: Johnson Matthey PLC, London (GB)

( * ) Notice: Subject to any disclaimer, the term of this patent is extended or adjusted under 35 U.S.C. 154(b) by 0 days.

(21) Appl. No.: 10/298,209

(22) Filed: Nov. 18, 2002

(65) Prior Publication Data

US 2003/0144556 A1 Jul. 31, 2003

Related U.S. Application Data

(63) Continuation of application No. PCT/GB01/02116, filed on May 14, 2001.

(30) Foreign Application Priority Data

May 18, 2000 (GB) ............................................. 0011858

(51) Int. Cl.$^7$ .......................... C07C 45/72; C07C 27/04
(52) U.S. Cl. ..................... 568/388; 568/396; 568/862
(58) Field of Search ................ 568/388, 396, 568/862

(56) References Cited

U.S. PATENT DOCUMENTS

| | | | |
|---|---|---|---|
| 3,886,219 A | * | 5/1975 | Reich |
| 4,086,188 A | * | 4/1978 | Reichle |
| 4,102,930 A | | 7/1978 | Deem .................. 260/593 |
| 4,165,339 A | * | 8/1979 | Reichle |
| 4,599,453 A | * | 7/1986 | Fragale et al. |
| 4,704,478 A | * | 11/1987 | Olson |
| 5,055,620 A | * | 10/1991 | Schutz |
| 5,059,724 A | * | 10/1991 | Chen et al. |

FOREIGN PATENT DOCUMENTS

| | | |
|---|---|---|
| EP | 0765853 | 4/1997 |
| JP | 62258335 | 11/1987 |
| JP | 63068538 | 3/1988 |
| JP | 63096146 | 4/1988 |
| JP | 63096147 | 4/1988 |

OTHER PUBLICATIONS

Di Cosimo et al. "Study of the Catalyst Deactivation in the Base–Catalyzed Oligomerization of Acetone" *Journal of Molecular Catalysis A: Chemical* 130 (1998) 177–185.

Chen et al. "One–step synthesis of methyl isobutyl ketone from acetone with calcined Mg/Al hydrotalcite–supported palladium or nickel catalysts" Applied Catalysis A: General 169 (1998) pp. 207–214.

Narayanan et al. "Selective hydrogenation of acetone to methyl isobutyl ketone (MIBK) over co–precipitated Ni/Al$_2$O$_3$ catalysts" Applied Catalysis A: General 145 (1996) pp. 231–236.

Lin et al. "Na promotion of Pd/MgO catalysts for low–pressure one–step synthesis of MIBK from acetone + H$_2$" Applied Catalysis A: General 147 (1996) L259–265.

Gandia et al. "Application of new hydrogenated aluminophosphate oxynitride (ALPON) as a catalytic support for the one–step synthesis of methyl isobutyl ketone from acetone" Applied Catalysis A: General 114 (1994) pp. L1–L7.

Gandia et al. "Highly selective one–step formulation of methyl isobutyl ketone from acetone with a magnesia supported nickel catalyst" Applied Catalysis A: General 101 (1993) pp. L1–L6.

Tanabe et al. "Addition of metal cations to magnesium oxide catalyst for the aldol condensation of acetone" Applied Catalysis, 48 (1989) pp. 63–70.

Kirk Othmer Encyclopedia of Chemical Technology, 4$^{th}$ ed., vol. 14, Wiley, New York (1996) pp. 989–991.

* cited by examiner

*Primary Examiner*—Johann Richter
*Assistant Examiner*—Sikarl A. Witherspoon
(74) *Attorney, Agent, or Firm*—Pillsbury Winthrop LLP

(57) ABSTRACT

Production of unsaturated ketones by the aldol condensation of ketones such as acetone or methyl ethyl ketone by contacting the ketone in the vapor phase with a particulate catalyst comprising at least one basic alkali metal compound supported on an inert substrate at a temperature above 175° C. The produce ketones may be hydrogenated to form saturated ketones or alcohols.

13 Claims, No Drawings

ALDOL CONDENSATION REACTION AND CATALYST THEREFOR

CROSS REFERENCE TO RELATED APPLICATION

This application is a continuation of International Application No. PCT/GB01/02116, filed May 14, 2001. This application, in its entirety, is incorporated herein by reference.

This invention relates to aldol condensation processes and in particular to the condensation of ketones.

The coupling reaction of relatively small molecules to form relatively large molecules is a commercially attractive route to form a range of products having specific structures and properties. As an example, Methyl isobutyl ketone (2-methyl-4-pentanone) is the largest volume aldol reaction product of acetone. Methyl isobutyl ketone (MIBK) is an excellent solvent for cellulose and resin based coating systems and also for vinyl, epoxy and acrylic resins. It is traditionally manufactured via a three-step reaction scheme as described in Industrial Organic Chemistry, $3^{rd}$ Edition (eds. K Weissermel and H J Arpe), Wiley (1997), p 280–281, the stages comprising (i) the base catalysed aldol condensation of acetone in the liquid phase to diacetone alcohol (DAA), (ii) the acid catalysed dehydration of DAA to mesityl oxide (MO) and (iii) the hydrogenation of MO to MIBK and further to methyl isobutyl carbinol.

These processes are complicated and the operating costs are high. The condensation equilibrium in step (i) does not favour aldol formation. In step (ii) acetone can be formed by the reaction of mesityl oxide with water and in step (iii) the less useful methyl isobutyl carbinol has to be separated by distillation. There is also a corrosive problem due to the use of liquid acids and bases.

Recently, a one-step process from acetone to MIBK has become commercially feasible and several catalytic systems have been described for this process. They mainly consist of palladium supported, for example, on $KOH-Al_2O_3$, $MgO-SiO_2$ or cation exchange resins (Kirk-Othmer Encyclopaedia of Chemical Technology, Vol. 13, Wiley, New York, 1979, p.907), $CaO-MgO-SrO-Al_2O_3$ as described in JP-A-62258335, $Nb_2O_5$ as described in JP-A-63096147; $ZrO(OH)_2$-carbon as described in JP-A-63068538 and Ce, Hf and/or Ta oxides or hydroxidescarbon as described in JP-A-63096146. Very high selectivities to MIBK (>90%) are described in the 80–160° C. range and acetone conversions near 40%. The high operating pressures required, typically 10–100 atm are a disadvantage of the single-step process.

GB-A-921510 describes a liquid-phase process for the condensation of acetone to make mesityl oxide using a catalyst which is an alkali-treated activated alumina. The process is favoured at low temperatures, between about 80 and 150° C.

Tanabe et al (*Applied Catalysis* 48 (1989) 63–70) describe the effect of various metal cations on the activity of magnesia catalysts in the liquid phase aldol condensation of acetone.

More recently, catalysts which operate efficiently in the gas phase at atmospheric pressure have been developed for the one-step process. These have included Pd/SAPO-34, described in U.S. Pat. No. 4,704,478, Pd/KH-ZSM-5 (in U.S. Pat. No. 5,059,724); Ni/MgO (L M Gandia et al, Appl. Catal. A: General, 101 (1993) L1–L6), Ni/ALPON (L M Gandia et al, Appl. Catal. A: General 114 (1994) L1–L7; Na/Pd/MgO (K Lin et al, Appl. Catal. A: General 147 (1996) L259–L265); $Ni/Al_2O_3$ (S Narayanan et al, Appl. Catal. A: General 145 (1996) 231–236) and Pd or Ni supported on Mg/Al hydrotalcites (Y Z Chen et al, Appl. Catal. A: General 169 (1998) 207–0214).

U.S. Pat. Nos. 4,086,188 and 4,165,339 describe the gas phase condensation of aldehydes and ketones, especially acetone in the presence of catalysts comprising a complex magnesium-aluminium oxide-hydroxide mixture which is doped with lithium ions. The reactions produce isophorone and mesityl oxide and achieve isophorone: mesityl oxide ratios>1.

U.S. Pat. No. 4,599,453 describes the single stage production of higher aliphatic ketones by reacting a starting ketone with carbon monoxide in the presence of a catalyst comprising copper supported on a metal oxide.

U.S. Pat. No. 5,055,620 describes a polymorphic magnesium-oxide-pseudoboehmite composition for the aldol condensation of acetone to isophorone.

In WO-A-00/31011, the aldol condensation of aldehydes in the gas phase was described using catalysts comprising an alkali metal on an inert support.

We have now found that the condensation of ketones can be effected in the gaseous phase using a solid base catalyst thereby avoiding the need for aqueous caustic solutions with their consequent handling and effluent disposal problems.

It is an object of the present invention to provide a method of forming a carbonyl compound by the aldol condensation of at least one organic ketone. It is a further object of the invention to provide a method of making a saturated ketone or an alcohol by the hydrogenation of a carbonyl compound formed by the aldol condensation of at least one organic ketone. It is a further object of the invention to provide a catalyst which is capable of catalysing the aldol condensation of at least one ketone to form a higher organic ketone.

According to the invention, we provide a process for the production of a product ketone containing at least six carbon atoms from at least one feedstock ketone by contacting the feedstock ketone in the vapour phase with a particulate catalyst comprising at least one basic alkali metal compound supported on an inert substrate at a temperature above 175° C.

According to a second aspect of the invention, we provide a process for the production of an alcohol by the hydrogenation of a ketone containing at least six carbon atoms which has been formed from at least one feedstock ketone by contacting the feedstock ketone in the vapour phase with a particulate catalyst comprising at least one basic alkali metal compound supported on an inert substrate at a temperature above 175° C.

According to a third aspect of the invention, we provide a catalyst for catalysing the aldol condensation of a ketone at a temperature above 175° C., said catalyst comprising at least one basic alkali metal compound supported on an inert substrate.

Suitable catalysts are basic sodium, potassium, or cesium compounds such as oxides hydroxides or carbonates supported on a material such as carbon, silica, alumina, a clay, silicalite or a zeolite Preferred catalysts are alkali metal compounds supported on silica, especially potassium or sodium supported on silica. The potassium and sodium catalysts appear to have high activity and are the most selective. The catalyst preferably contains 0.1 to 25%, preferably 0.4 to 18%, by weight of the alkali metal.

The support preferably is in the form of particles having maximum and minimum dimensions in the range 0.5 to 10 mm, preferably 1 to 4 mm, and having a BET surface area in the range 50 to 500 m²/g. The catalyst is preferably made by impregnating the support particles with an aqueous solution of an alkali metal compound that is basic or decomposes to a basic compound upon heating, for example an alkali metal hydroxide, acetate, oxalate, nitrate or carbonate, followed by drying and calcination if necessary to effect decomposition to a basic compound.

The reaction is effected at temperatures above 175° C., particularly above 200° C., and preferably below 450° C., particularly in the range 200 to 350° C. As the temperature increases the activity increases but the selectivity tends to decrease, often with the production of hydrogenated products.

After a period of operation, the activity of the catalyst tends to decrease through the deposition of carbon as a result of side reactions. The catalyst may be periodically regenerated by burning off the carbon by heating in an oxygen-containing atmosphere, e.g. air or oxygen or air diluted with an inert gas such as nitrogen. The catalyst may be disposed as a fixed bed or a fluidised bed may be employed. In the latter case a portion of the catalyst may be continuously withdrawn and regenerated and returned to the reaction zone.

The main product of the condensation is an unsaturated ketone. Often it is desired to hydrogenate the product to the corresponding saturated ketone or its corresponding saturated alcohol. This may be effected by passing the products, possibly after separation of the starting ketone that has not reacted, together with hydrogen, through a bed of a suitable hydrogenation catalyst, such as copper or a platinum group metal, on a suitable support The temperature at which the hydrogenation is effected will often be below that used for the aldol condensation. The reaction mixture from the aldol condensation may be cooled to the desired hydrogenation temperature by addition of a suitable quench gas, such as cool hydrogen.

As indicated above, the primary product from the condensation is the unsaturated ketone, e.g. mesityl oxide. In some cases, the desired product is not the corresponding alcohol but is the corresponding saturated ketone, e.g. MIBK. The unsaturated ketone may be hydrogenated to the saturated ketone using a hydrogenation catalyst, such as palladium, that selectively hydrogenates the carbon-carbon double bond compared with the carbonyl group. This means that the catalyst effects hydrogenation of the carbon-carbon double bond but does not effect hydrogenation of the carbonyl group to any significant extent. Suitable catalysts may be easily selected by the skilled person.

In some cases it may be possible to effect the condensation and hydrogenation in a single stage by formulating the base catalyst also to have the appropriate hydrogenation activity and co-feeding hydrogen with the ketone to the reaction zone. Such a base/hydrogenation catalyst may be a mixture of separate particles of base and hydrogenation catalyst, or may be particles of the support impregnated with both a base and a material having hydrogenation activity. However, it has been found that where the condensation and hydrogenation is effected in a single stage, e.g. by the use of a catalyst having both the condensation and hydrogenation activity, the condensation activity of the catalyst may decrease relatively rapidly. Therefore it is preferred to effect such condensation and hydrogenation in separate stages, e.g. by using a bed of the condensation catalyst, followed by a bed of the hydrogenation catalyst. In this case it is preferred that the condensation catalyst is free from components, such as copper, and Group VIII metals, giving hydrogenation activity.

Regioselective reactions of unsymmetrical ketones are of fundamental importance in organic synthesis, the most familiar reactions being α-alkylations, Michael additions and aldol condensations. In the presence of a base, methyl ethyl ketone, the simplest of the higher ketones, is capable of losing a proton from the adjacent methylene group or the terminal methyl group. Tautomerisation of the two possible carbanions formed from the proton abstraction leads to two regioisomeric enolates. The less substituted enolate 1 is formed by

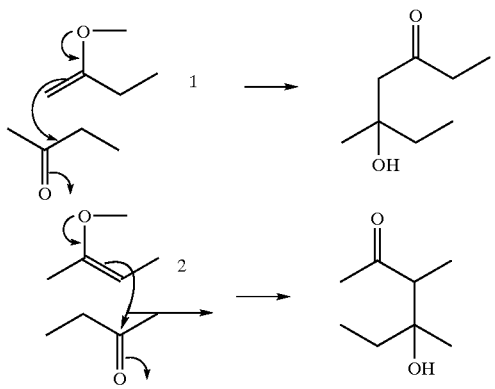

irreversible kinetic control, whereas those reactions under thermodynamic control usually yield the more substituted product 2. In more favourable cases one regioisomer can greatly predominate in the equilibrium mixture but often the equilibrium constant is not sufficiently high to achieve an acceptable regioselectivity. The enolates formed can then attack a polarised carbonyl group to form a carbon-carbon bond to form two aldol products. We have found that when the feedstock ketone is not symmetrical, e.g. methyl ethyl ketone, so that the aldol condensation is capable of forming either terminal or internal unsaturation, the catalysts described herein are capable of producing a reaction product which is relatively rich in the terminally unsaturated product, i.e. the catalysts are selective to produce mainly one isomer, both cis and trans forms of this isomer being formed.

The invention is illustrated by the following examples.

EXAMPLE 1

Preparation of the Catalyst

The catalysts were made by impregnating a gel silica in the form of spheres of diameter in the range 2–4 mm having a purity of over 99%, a total surface area of about 300–350 m²/g, and a pore volume of 1.04 cm³/g with 76% of the pore volume provided by pores having a diameter in the range 7–23 nm with aqueous solutions of alkali metal nitrates before drying for 12 hours at 100° C. and calcining at 450° C. for 3 hours to obtain catalysts containing various loadings of the alkali metal oxide.

EXAMPLE 2

A catalyst prepared as described in Example 1 and containing 4% by weight of sodium as sodium oxide on silica was used for the aldol condensation of butan-2-one (MEK) at varying temperatures by passing a mixture of MEK in nitrogen at a flow rate of 0.05 ml/min entrained in nitrogen at a gas flow rate of 50 ml/min through a fixed bed of 4 ml of the catalyst at a pressure of 5 bar gauge at temperatures between 325 and 400° C. The products were analysed by gas chromatography-mass spectroscopy using 6-methyl-5- hepten-2-one and diphenyl ether as an internal standard. The results are given in Table 1 as conversion and selectivity, calculated as follows:

% Conversion=Σ[products (as moles of butan-2-one)]/[butan-2-one]$_{initial}$×100

% Selectivity=[product]/Σ[products]×100.

EXAMPLE 3

Example 2 was repeated using a catalyst containing 4% by weight of Cs instead of Na as caesium oxide. The results are shown in Table 1.

The major product from Example 2 and Example 3 was 5-methyl-4hepten-3-one, with both isomers being formed.

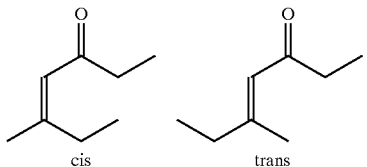

cis     trans

This indicates an initial proton abstraction from the terminal methyl group of MEK. This is followed by the dehydration of the aldol intermediate to form conjugated products. Only very low levels of the 3,4-dimethyl-4-hexen-2-one product formed via the other enolate were detected. Two further terminal condensation products, thought to be cis and trans 5-methyl-5-hepten-3-one with molecular weight of 126 were also detected. The presence of 3-methyl-3-hepten-2-one was detected, which may be the result of isomerisation.

Some trimers (molecular weight 180 species) were also detected in the product stream. Increasing the temperature tended to result in the loss of two trimeric species but with a rise in a third, possibly due to isomerisation to the stable trimer. This stable isomer may be a cyclic ketone and therefore resistant to further condensation.

EXAMPLE 4

The reaction described in Example 2 was repeated using a catalyst bed comprising 2 ml of the 4% Na catalyst followed by 2 ml of a copper oxide/zinc oxide hydrogenation catalyst made by co-precipitation and containing 35% by weight of copper oxide. This secondary bed was activated at 200° C. under increasing levels of hydrogen. The experiment was performed under 100% hydrogen and reaction temperature was varied between 300 and 375° C. The results are shown in Table 1.

The products were found to contain essentially two main components; 5-methylheptan-3-one and 5-methylheptan-3-ol. The former is merely the partially hydrogenated form of the latter and therefore both compounds can be regarded as being derived from the kinetically controlled aldol product 5-methyl-4-hepten-3-one or cis and trans-5-methyl-5-hepten-3-one because subsequent hydrogenation of these compounds would result in the formation of 5-methylheptan-3-ol.

Increasing the temperature reduced the efficiency of the hydrogenation step evidenced by an increase in the level of the partially hydrogenated compound, 5-methylheptan-3-one, without a concomitant increase in the formation of the fully hydrogenated molecule, 5-methylheptan-3-ol. This may be overcome by increasing the hydrogen pressure of the system.

The combined catalyst bed of Example 4 appeared to be more active and selective to the terminal aldol products than the base catalysts alone, as used in Examples 2 and 3. This result is surprising considering that only 2 ml of the Na/SiO$_2$ catalyst bed was used compared with 4 ml of the same catalyst in Example 2. Furthermore, it is notable that no trimeric species were detected in the product stream.

EXAMPLE 5

Comparative

The reaction was repeated using 4 mls of the copper/zinc hydrogenation catalyst used in Example 4. The catalyst was pre-reduced as described above but prior to introduction of the MEK the reactor was purged of hydrogen and the reaction was performed under an inert nitrogen atmosphere. The products showed little evidence of aldol condensation compounds. The major compounds formed had a molecular weight of 138 and are believed to be the product of a dehydrogenation reaction of two MEK molecules, bicyclo-[3,3,0]-octane-3,7-dione, which can exist as cis and trans isomers and was produced at consistent levels throughout the course of the experiment regardless of temperature changes.

TABLE 1

| Catalyst | Temp (° C.) | % Conversion | % Selectivity to terminal dimeric products | % Selectivity to trimeric products |
|---|---|---|---|---|
| Example 2 | 325 | 1.32 | 67.4 | 18.3 |
| Na/SiO$_2$ | 350 | 4.06 | 88.1 | 9.1 |
| | 375 | 6.51 | 89.4 | 9.1 |
| | 400 | 7.83 | 86.0 | 12.5 |
| Example 3 | 325 | 2.64 | 83.0 | 12.8 |
| Cs/SiO$_2$ | 350 | 4.37 | 88.5 | 10.2 |
| | 375 | 5.90 | 87.6 | 11.1 |
| | 400 | 4.27 | 87.2 | 11.3 |
| Example 4 | 300 | 4.47 | 97.4 | None detected |
| Na/SiO$_2$ + | 325 | 7.73 | 97.8 | None detected |
| Cu/Zn | 350 | 10.06 | 96.6 | None detected |
| | 375 | 10.58 | 98.9 | None detected |

EXAMPLE 6

A catalyst comprising 4% by weight (as oxide) of potassium on silica was prepared by the method described in Example 1. A reactor tube was charged with 3 mls of the K/SiO$_2$ catalyst followed by a 3 ml bed of a hydrogenation catalyst comprising 1% palladium on carbon. The Pd/C catalyst was reduced before use at 50° C. under a 10% H$_2$/N$_2$ stream of 50 mls/min at 3 barg for 18 hours. Acetone vapour in hydrogen was fed to the reactor at an acetone feed rate of 0.05 mls/min and a H$_2$ flow rate of 62 ml/min. The products were collected and analysed by gas chromatography for conversion and selectivity calculations. The GC was calibrated using acetone, MIBK, mesityl oxide (MO) and isophorone (ISO). The following equations were used to calculate conversion and selectivity results shown in Table 2.

Conversion (%) =

$$\frac{\text{moles of actone in feed} - \text{moles of acetone in sample}}{\text{moles of acetone in feed}} \times 100\%$$

-continued $$\text{Selectivity (\%)} = \frac{(2 \times \text{moles MIBK} + 2 \times \text{moles MO} + 3 \times \text{moles ISO})}{(\text{moles acetone in feed} - \text{moles actone in sample})} \times 100\%$$

TABLE 2

| Run time (hrs) | Pressure (bar) | Conversion (%) | Selectivity (%) | Ratio of main products (%) | | |
|---|---|---|---|---|---|---|
| | | | | MIBK | MO | ISO |
| 3 | 5 | 17.0 | 78.0 | 67.7 | 19.1 | 13.1 |
| 19 | 5 | 15.5 | 82.3 | 63.4 | 24.3 | 12.4 |
| 42 | 7 | 15.6 | 89.2 | 64.9 | 21.2 | 13.9 |
| 49 | 9 | 14.4 | 93.3 | 67.8 | 19.7 | 12.6 |
| 68 | 9 | 15.0 | 93.8 | 68.1 | 19.3 | 12.6 |

What is claimed is:

1. A process for the production of a product ketone containing at least six carbon atoms comprising subjecting at least one feedstock ketone to aldol condensation by contacting the feedstock ketone in the vapor phase with a particulate catalyst comprising at least one basic alkali metal compound supported on an inert substrate selected from the group consisting of carbon, silica, alumina, a clay, silicalite, or a zeolite, at a temperature above 175° C.

2. A process according to claim 1 wherein the catalyst comprises a basic alkali metal compound supported on silica.

3. A process according to claim 1 wherein the catalyst comprises a basic alkali metal compound supported on alumina.

4. A process according to claim 1 wherein the catalyst contains 0.1–25% by weight of the alkali metal.

5. A process according to claim 1 wherein the inert substrate is in the form of particles having maximum and minimum dimensions in the range 0.5 to 10 mm and having a BET surface area in the range 50 to 500 m²/g.

6. A process according to claim 1 wherein the reaction is effected at a temperature above 200° C.

7. A process according to claim 6 wherein the reaction is effected at a temperature in the range 200° C. to 350° C.

8. A process according to any one of claim 1 wherein the feedstock ketone is acetone or methyl ethyl ketone.

9. A process according to claim 1, wherein the particulate catalyst comprising at least one basic alkali metal compound supported on an inert substrate is periodically regenerated by heating in an oxygen-containing atmosphere.

10. A process according to claim 1 wherein the product of the aldol condensation is at least partially hydrogenated to give a saturated ketone by means of a catalyst which selectively hydrogenates carbon-carbon double bonds compared with carbonyl groups.

11. A process according to claim 10 wherein the aldol condensation and hydrogenation are effected in separate stages by passing the feedstock ketone through a bed of a particulate catalyst comprising at least one basic alkali metal compound supported on an inert substrate at a temperature above 175° C., and then passing the reaction products together with hydrogen through a bed of a hydrogenation catalyst.

12. A process for the production of an alcohol or mixture of alcohols comprising producing a ketone containing at least six carbon atoms by subjecting at least one feedstock ketone to aldol condensation by contacting the feedstock ketone in the vapor phase with a particulate catalyst comprising at least one basic alkali metal compound supported on an inert substrate selected from the group consisting of carbon, silica, alumina, a clay, silicalite, or a zeolite, at a temperature above 175° C., and then hydrogenating said ketone.

13. A process according to claim 12 wherein the aldol condensation and hydrogenation are effected in separate stages by passing the feedstock ketone through a bed of a particulate catalyst comprising at least one basic alkali metal compound supported on an inert substrate at a temperature above 175° C., and then passing the reaction products together with hydrogen through a bed of a hydrogenation catalyst.

* * * * *